US008741626B2

United States Patent
Chi et al.

(10) Patent No.: US 8,741,626 B2
(45) Date of Patent: Jun. 3, 2014

(54) **MUTANT STRAIN OF *ASPERGILLUS SETAE* WITH ENHANCED PROTEASE ACTIVITY AND PREPARATION METHOD OF NATURAL TASTE ENHANCER USING THE SAME**

(75) Inventors: Hyun Chi, Seoul (KR); Seong-Jun Cho, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 143 days.

(21) Appl. No.: 13/497,039

(22) PCT Filed: Oct. 29, 2009

(86) PCT No.: PCT/KR2009/006306
§ 371 (c)(1),
(2), (4) Date: Mar. 19, 2012

(87) PCT Pub. No.: WO2011/046249
PCT Pub. Date: Apr. 21, 2011

(65) Prior Publication Data
US 2012/0178125 A1    Jul. 12, 2012

(30) Foreign Application Priority Data
Oct. 16, 2009 (KR) .................. 10-2009-0098528

(51) Int. Cl.
*C12N 9/62* (2006.01)
*C12N 1/20* (2006.01)
*C12N 1/00* (2006.01)

(52) U.S. Cl.
USPC ............... 435/254.3; 435/225; 435/256.1

(58) Field of Classification Search
CPC ............ C12N 1/14; C12N 1/22; C12P 21/06; C12R 1/66
USPC ................. 435/254.3, 25, 256.12
See application file for complete search history.

(56) References Cited

U.S. PATENT DOCUMENTS

2001/0049118 A1* 12/2001 Umitsuki et al. ............... 435/41

FOREIGN PATENT DOCUMENTS

| JP | 03-277289 | 12/1991 |
| JP | 07-222584 | 8/1995 |
| JP | 07-274944 | 10/1995 |
| JP | 08-173085 | 7/1996 |
| JP | 08-242810 | 9/1996 |
| JP | 10-210967 | 8/1998 |

OTHER PUBLICATIONS

Minami et al. (2003) "A mutant *Bacillus subtilis* γ-glutamyltranspeptidase specialized in hydrolysis activity" FEMS Microbiology Letters 224: 169-173.
Nemoto et al. (2009) "Isolation of *Aspergillus oryzae* mutants for heterologous protein production from a double proteinase gene disruptant" Applied Genetics and Molecular Biotechnology 82: 1105-1114.
H. Sekine et al., Agric. Biol. Chem., 1969, vol. 33, No. 10, pp. 1477-1482, "Isolation of Highly Proteolytic Mutants from *Aspergillus sojae*".
S. Ueno et al., Appl, Microbiol. Biotechnol, 1987, vol. 26, pp. 273-276, "Secretory enzyme production and conidiation of *Aspergillus oryzae* in submerged liquid culture".
S. Yamamoto et al., J. Ferment. Technol. 1974, vol. 52, No. 8, pp. 564-569, "Production of Glutaminase by *Aspergillus sojae*".
S. Ushijima et al., Agric. Biol.Chem. 1987 ,vol. 51, No. 4, pp. 1051-1057, Breeding by Protoplast Fusion of *Koji* Mold, *Aspergillus sojae*.
S. Ushijima et al., Agric. Biol. Chem. 1987, vol. 51, No. 10, pp. 2781-2786, "Improvement of Enzyme Production through Mutation or Haploidization of Heterozygous Diploids Obtained by Protoplast-fusion of *Aspergillus sojae*".
S. Ushijima et al., Agric. Biol. Chem. 1990, vol. 54, No. 7, pp. 1667-1676, "Breeding of New *Koji*-molds through Interspecific Hybridization between *Aspergillus oryzae* and *Aspergillus sojae* by Protoplast Fusion".
S. Ushijima et al., Agric. Biol. Chem. 1991, vol. 55, No. 1, pp. 129-136, "Interspecific Electrofusion of Protoplasts between *Aspergillus oryzae* and *Aspergillus sojae*".
T. Nakadai et al., J. Ferment. Technol. 1977, vol. 55, No. 3, pp. 273-276, "Hyproduction of Peptidase and Proteinase by Mutants of *Aspergillus oryzae*".
T. Yano et al., Agric. Biol. Chem. 1991, vol. 55, No. 2, pp. 379-385, "Development of a Soft Gel Cultivation Method".

* cited by examiner

*Primary Examiner* — Michele K Joike
(74) *Attorney, Agent, or Firm* — Swanson & Bratschun, LLC

(57) ABSTRACT

The present invention relates to a mutant strain of *Aspergillus sojae* with an enhanced protease activity and a preparation method of a natural taste enhancer using the same. More specifically, the present invention relates to the mutant strain of *Aspergillus sojae* with an enhanced protease activity is obtained by selecting a strain with high protease activity and treating it with N-methyl-N'-Nitroso-N-nitrosoguanidine (NTG) and inducing a mutation through irradiating, and a preparation method of a natural taste enhancer using protein hydrolysate obtained by hydrolyzing the protein sources with their cultures.

4 Claims, No Drawings

MUTANT STRAIN OF ASPERGILLUS SETAE WITH ENHANCED PROTEASE ACTIVITY AND PREPARATION METHOD OF NATURAL TASTE ENHANCER USING THE SAME

CROSS-REFERENCE TO RELATED APPLICATION

This application is a 35 U.S.C. §371 national phase application of PCT/KR2009/006306, filed Oct. 29, 2009 (WO 2011/046249), entitled "Mutant Strain of *Aspergillus sojae* with Enhanced Protease Activity and Preparation Method of Natural Taste Enhancer Using the Same." PCT/KR2009/006306 is a non-provisional of Korean patent application No. 10-2009-0098528, filed Oct. 16, 2009, which is incorporated by reference herein in its entirety.

BACKGROUND

1. Field of the Invention

The present invention relates to a mutant strain of *Aspergillus sojae* with an enhanced protease activity and a method of preparing a natural taste enhancer using the same.

2. Discussion of Related Art

*Aspergillus oryzae* and *Aspergillus sojae*, which are *Aspergillus* sp. used when preparing soy sauce, Doenjang (traditional fermented soybean paste) and the like, produce an enzyme such as protease, amylase, glutaminase, and the like. Protease degrades protein into peptide and amino acid, and glutaminase plays an important role in flavoring soy sauce, Doenjang, and the like, by converting free glutamine into tasty glutamic acid when degrading protein.

Therefore, researches are being carried out to improve an enzyme activity of protease or glutaminase that plays an important role in flavoring. There are the methods that microorganism is mutated through UV irradiation, a mutagen treatment, and an irradiation to isolate a mutant strain with high activity (H. Sekine et al, *Agric. Biol. Chem.*, 33, 1477 (1969), S. Nasuno et al, *J. Ferment. Technol.*, 55, 273 (1977), S. Yamamoto et al, *J. Ferment. Technol.*, 52, 564 (1974)), or a high activity strain, in which all of two enzymes' activities are high, is manufactured by a cell fusion technique (Shingeomi Ushijima et al, *Agric. Biol. Chem.*, 51 (4), 1051-1057 (1987), Shingeomi Ushijima et al. *Agric. Biol. Chem.* 51; 2781-2786 (1987), Shingeomi Ushijima et al. *Agric. Biol. Chem.* 54; 1667-1676, (1990), Shigeomi Ushijima et al. *Agric. Biol. Chem.*, 55 (1), 129-136, (1991)).

Soy sauce and Doenjang are difficult to be widely used in food because contamination of various germs by fermenting it in a solid state cannot be avoided and thus high concentration table salt should be added. Therefore, the researches for using them as seasonings are being carried out with excluding the contamination of various germs by culturing a strain in a liquid state, and then with applying the culture medium to protein without adding a table salt (JP Patent Publication Nos. 8-173085 A and 8-242810 A).

As the researches progress, the researches for producing protease or glutaminase during liquid culture of *Aspergillus oryzae* and *Aspergillus sojae* are also being carried out (S. Ueno et al, *Appl, Microbiol. Biotechnol.*, 26, 273 (1987), JP Patent Publication No. 3-277289 A, T. Yano et al, *Agric. Biol. Chem.*, 55 (2), 379 (1991), JP Patent Publication No. 10-210967 A).

However, most of them have a low activity level. Even though glutaminase has very high activity, glutamine should be firstly cleaved by protease activity in order to expect an effect of glutaminase which converting glutamine into glutamic acid and thereby giving a savory taste to food.

SUMMARY OF THE INVENTION

Accordingly, the present inventor prepared a mutant strain of *Aspergillus sojae* with an enhanced protease activity in order to prepare a protein hydrolysate with high content of glutamic acid, and could prepare a natural taste enhancer with a savory taste as a result of hydrolyzing protein using the same.

Therefore, an object of the present invention is to provide a mutant strain of *Aspergillus sojae* with an enhanced protease activity.

In addition, other object of the present invention is to provide a method of preparing a natural taste enhancer using the mutant strain of *Aspergillus sojae* as mentioned above.

In order to achieve the above objects, the present invention provides a mutant strain of *Aspergillus sojae* with an enhanced protease activity, which is derived from *Aspergillus sojae* CJCC_011057P (KCCM-11043P), by treating N-methyl-N'-Nitroso-N-nitrosoguanidine (NTG) and inducing a mutation through irradiating.

In addition, the present invention provides a method of preparing a natural taste enhancer, comprising: (a) culturing a mutant strain of *Aspergillus sojae*; (b) hydrolyzing protein sources by adding the culture obtained from the above (a); and (c) concentration/drying and powdering the hydrolyzed protein solution obtained from the above (b).

As mentioned above, the mutant strain of *Aspergillus sojae* according to the present invention has higher protease activity than that of its parent strain. The protein hydrolysate obtained by hydrolyzing the protein sources with their cultures has high degree of degradation and high content of glutamic acid so that it can be used as a natural taste enhancer with a rich flavors and a savory taste as compared with the conventional protein hydrolysates when applying it in food.

DETAILED DESCRIPTION OF EXEMPLARY EMBODIMENTS

Hereinafter, the present invention will be described in detail.

The present invention provides a mutant strain of *Aspergillus sojae* with an enhanced protease activity, by selecting a strain with high protease activity and treating it with N-methyl-N'-Nitroso-N-nitrosoguanidine (NTG) and inducing a mutation through irradiating.

Microorganisms producing a protease are isolated from a sample, such as a block of fermented soybean, Doenjang, soy sauce, and the like, obtained from all across the country, and then pure culture of strains with high protease activity from among these are used as a parent strain for the present invention. Preferably, the parent strain used for the present invention may be *Aspergillus sojae* CJCC_011057P (KCCM-11043P).

For the present invention, a method of inducing a mutation may include a method of inducing a chemical mutation with a mutagen such as N-methyl-N'-Nitroso-N-nitrosoguanidine (NTG), hydroxylamine, nitric oxide, ethyl methane sulfonate (EMS), dimethyl sulfate, and the like; a method of inducing a mutation through irradiating UV, X-ray, a radiation, and the like; a spontaneous mutation obtained without a mutation treatment; and the like.

For the present invention, the above-isolated *Aspergillus sojae* is treated with N-methyl-N'-Nitroso-N-nitrosoguanidine (NTG) that is frequently and generally used as a mutagen, and then irradiated so that a mutant strain with good growth and high protease activity can be obtained by selection. The protease activity of the mutant strain of *Aspergillus sojae* with high protease activity according to the present invention is about 5-8 times higher than that of a parent strain. Preferably, the mutant strain of *Aspergillus sojae* according to the present invention may be *Aspergillus sojae* CJCC__080124P (KCCM-11026P).

Also, the present invention provides a method of preparing a natural taste enhancer, comprising: (a) culturing a mutant strain of *Aspergillus sojae*; (b) hydrolyzing protein sources by adding the culture obtained from the above (a); and (c) concentration/drying and powdering the hydrolyzed protein solution obtained from the above (b).

The protein sources include, for example, a soybean, wheat, corn meal, rice, fish meal, milk casein, collagen, and the like. In addition, defatted soybean, isolated soy protein, wheat gluten, corn gluten, defatted rice bran, rice protein, fish protein and various proteins obtained from a process such as defatting, puffing, or solubilizing, or isolated protein obtained from such various proteins can be used.

The hydrolysis may be performed by using the culture obtained from culturing the mutant strain of *Aspergillus sojae* according to the present invention.

The culture of the mutant strain of *Aspergillus sojae* according to the present invention may be preferably used as liquid cultures as it is, but enzyme which is isolated and purified from the culture also may be used as necessary. That is, the enzyme which is prepared by separating the cell from the liquid cultures through centrifugation or filtration and precipitating the protein from the cell lysate or culture solution using conventional separation method, for example, a salting out method, an isoelectric precipitation, a solvent precipitation, and the like, and concentrating the resultant using ultrafiltration, may be used. In addition, refined products that are isolated and then collected by a general purification method may be used by alone or combination.

A commercially available enzyme formulation, for example, enzyme solution or enzyme formulation containing proteinase, lysozyme, glutaminase, and the like, may be added to the culture depending on the purpose.

As the condition of the hydrolysis, the culture of the mutant strain of *Aspergillus sojae* is added to defatted soybean, wheat gluten, and the like and preferably reacted at 20~60° C. for 6 hours to 15 days. Preferably, it is reacted at 30~50° C. for 24 hours to 10 days.

After terminating the hydrolysis, the protein that is not completely hydrolyzed and insoluble materials among the protein hydrolysates may be removed out by a general preparation method such as a centrifugation or a filtration, and then the separated liquid phase is powdered after concentration/drying.

The protein hydrolysates according to the method of the present invention has high degree of degradation and high content of glutamic acid thereby exhibiting a rich flavors and a savory taste according to the results of measuring the content of free amino acid, the content of glutamic acid, and the content of total nitrogen.

EXAMPLE

Example 1

Isolation and Selection of Strain 5 g of each sample, such as a block of fermented soybean, Doenjang (traditional fermented soybean paste), soy sauce, and the like, collected from all across the country was serial-diluted; 0.1% Tween 80 was added; and then the diluted samples were spread onto a minimal agar plate (Czapek dox agar) containing 0.1% Triton X-100. They were incubated at 30° C. for 3 to 4 days and then the strains with large clear zone around colonies were isolated.

The isolated strains were again inoculated on a minimal liquid medium (Czapek dox broth; $NaNO_3$ 0.3%, $K_2HPO_4$ 0.1%, $MgSO_4.7H_2O$ 0.05%, KCl 0.05%, $FeSO_4.7H_2O$ 0.001%, sucrose 3%), and then cultured for 30° C. for 3 to 4 days. The cells are removed by a centrifugation and the supernatant was collected and then the proteolytic ability was measured and compared by using casein as a substrate.

The strains with excellent proteolytic ability were selected among the strains, and inoculated on a Potato dextrose agar (PDA) slant medium, and then cultured at 30° C. for 4 to 7 days. Since then, spore suspension was obtained (Number of Spore: about $1 \times 10^6$/ml), 0.1 ml of the spore suspension was spread onto a screening medium of protease activity (2% powdered skim milk, 0.5% $KH_2PO_4$, 1% glucose, 0.1% Triton X-100, 2% agar), and then incubated at 30° C. for 3 to 4 days to select the strain with large clear zone. The selected strain was inoculated into a minimal liquid medium containing 1% powdered skim milk, and shaking-cultured at 30° C. for 3 to 4 days, and then the cells were removed. The strain with highest protease activity was selected.

The selected strain was called '*Aspergillus sojae* CJCC__011057P,' and deposited with Deposit No. KCCM 11043P dated on Oct. 8, 2009 to Korean Culture Center of Microorganisms (KCCM) affiliated with Korea Federation of Culture Collection (KFCC), where is International Depositary Authority in 361-221, Hongjae 1-dong, Suseodaemun-gu, Seoul, Korea.

Example 2

Improvement of Strain of *Aspergillus Sojae*

(1) NTG Mutation

*Aspergillus sojae* CJCC__011057P (KCCM 11043P) as mentioned above was cultured on a PDA slant medium to obtain spore suspension. 3 mg/ml of N-methyl-N'-Nitroso-N-nitrosoguanidine (NTG) solution was mixed with the same amount of the spore suspension and then incubated at 30° C. for 1 hour.

The spore suspension was spread onto a PDA medium to select survival colonies and then the selected survival colonies were cultured on PDA slant medium at 30° C. for 4 to 7 days. About at least 1,000 mutant strains were selected, and then cultured in liquid medium (3% defatted soybean, 0.5% $KH_2PO_4$, 1.5% yeast extract, 1.5% glucose, 0.05% magnesium sulfate) at 30° C. for 48 hours to measure protease activities. As the results of measuring protease activities, the strains with high activity were selected and then mutations in the strains were sequentially induced.

(2) Irradiation Mutation

About at least 200 mutant strains with high protease activity, which were selected after the NTG mutation, were cultured on PDA slant medium to obtain spore suspension, and then irradiated with 0.3 KGy for 1 hour. The spore suspension were spread onto PDA medium to select survival colonies and then the selected survival colonies were cultured on PDA slant medium at 30° C. for 4 to 7 days.

About at least 1,000 mutant strains were selected and then cultured in liquid medium (3% defatted soybean, 0.5%

KH$_2$PO$_4$, 1.5% yeast extract, 1.5% glucose, 0.05% magnesium sulfate) at 30° C. for 48 hours to measure protease activities.

Example 3

Measurement of Protease Activity of Selected Mutant Strain

A protease activity was measured according to Anson-Hagihara's method (B. Hagihara et al., 1958, *J. Biochem.* 45 (1958), 185-94.) using casein as a substrate.

400 µl of 0.75% casein solution and 100 µl of 0.24 M Na$_2$HPO$_4$ solution (pH 7.5) were pre-incubated at 37° C. for 5 minutes; and 100 µl of culture solution of each selected mutant strain was added; and then cultured at 37° C. for 10 minutes. 600 µl of mixture solution that was mixed with the same amounts of (1) 0.1 M TCA (2) 0.22 M sodium acetate, and (3) 0.33 M acetic acid was added in order to stop the reaction. 200 µl of the supernatant of the reaction solution was added to 500 µl of 0.55 M sodium carbonate solution, then 100~500 µl of a commercially available phenol reagent that was diluted twice was added, and then stirred. Since then, it was cultured at 30° C. for 30 minutes and measured at 660 nm of absorbance. An amount of enzyme that produce non-protein Folin's TS-colorable substance equivalent to 1 µg of tyrosine per 1 minute was defined as 1 U.

As the result of inducing the mutation by the above method, a mutant strain A with good growth and high enzyme activity was selected. It was called 'Aspergillus sojae CJCC__080124P,' and deposited with Deposit No. KCCM 11026P dated on Aug. 14, 2009 to Korean Culture Center of Microorganisms (KCCM) affiliated with Korea Federation of Culture Collection (KFCC), where is International Depositary Authority in 361-221, Hongjae 1-dong, Suseodaemun-gu, Seoul, Korea.

As the result of comparing a protease activity of the mutant strain of *Aspergillus sojae* CJCC-080124P (KCCM 11026P) with that of its parent strain, its activity was about 6 folds higher than that of its parent strain. The result was 3~8 folds higher than 200~450 unit of protease activity of *Aspergillus oryzae* FERM P-14259 that was the mutant strain with high activity used in the conventional JP Patent Publication Nos. 8-242810 A and 7-274944 A, and higher than 1,000 U/ml of protease activity of *Aspergillus oryzae* J117331 (FERM P-15956) that was the mutant strain with high protease activity as disclosed in JP Patent Publication No. 10-210967 A. Accordingly, the protease activity of the mutant strain of *Aspergillus sojae* CJCC-080124P (KCCM 11026P) was of the highest level as compared with the protease activities of mutant strains with high activity as disclosed in the conventional Patents or articles.

The present invention used many kinds of mutagen treatments and various mutation methods when a strain was modified in order to develop a strain with at least 1,000 U/ml that was considered as nearly threshold values of protease activity when culturing in a liquid medium. However, there was a limit to make the strain that was already improved in a high level to have the activity of over 1,000 U/ml. Therefore, several irradiations were further performed to repeat the improvements, and finally the mutant strain with 1,800 U/ml activity could be obtained.

TABLE 1

| Strain | Protease Activity (U/ml) |
|---|---|
| *Aspergillus sojae* CJCC__011057P(Parent Strain) | 300 |
| *Aspergillus sojae* CJCC__08124P(Mutant Strain) | 1800 |

Example 4

Preparation of Protein Hydrolysate 800 ml of distilled water was added to 500 g of defatted soybean and then sterilized at 121° C. for 20 minutes to prepare the solution. Since then, 2,000 ml of the cultures of *Aspergillus sojae* CJCC__080124P (KCCM 11026P), the mutant strain and *Aspergillus sojae* CJCC__011057P (KCCM 11043P), the parent strain were mixed with the above solutions, respectively and then reacted at 40° C. for 10 days. Once reacting, a commercially available enzyme, i.e., 0.05% of glutaminase (amino enzyme INC) was added to increase the content of glutamic acid. The analysis result of the filtrate was disclosed in the following Table 2.

After completing the reaction, the enzyme was deactivated by heating at 85° C. for 20 minutes; cooled; and then centrifuged at 6,000 rpm for 20 minutes to obtain the supernatant. The supernatant was vacuum-concentrated, and then powdered by spray drying.

TABLE 2

| Assay Item | *Aspergillus sojae* CJCC__08124P (Mutant Strain) | *Aspergillus sojae* CJCC__011057P (Parent Strain) |
|---|---|---|
| Glutamic Acid(%) | 0.64 | 0.14 |
| Total Nitrogen(%) | 1.04 | 0.78 |
| Free Amino Acid(%) | 3.38 | 0.85 |

As shown in the above Table 2, the content of free amino acid and the content of total nitrogen as well as the content of glutamic acid were all high in the culture of the mutant strain as compared with those of the parent strain. Consequentially, since the protein hydrolysate obtained from the present invention has high degree of degradation and high content of glutamic acid thereby having rich flavor and savory taste, its use value was highly evaluated.

What is claimed is:

1. A mutant strain of *Aspergillus sojae* CJCC__080124P with an enhanced protease activity, which is derived from *Aspergillus sojae* CJCC__011057P (KCCM-11043P), by treating N-methyl-N'-Nitroso-N-nitrosoguanidine (NTG) and inducing a mutation through irradiating.

2. A method of preparing a natural taste enhancer, comprising:
   (a) culturing a mutant strain of *Aspergillus sojae* of claim 1;
   (b) hydrolyzing protein sources by adding the culture obtained from the above (a); and
   (c) concentration/drying and powdering the hydrolyzed protein solution obtained from the above (b).

3. The method of claim 2, wherein an enzyme solution or enzyme formulation containing proteinase, lysozyme, or glutaminase further added to the culture.

4. The method of claim 2, wherein the hydrolysis is reacted at 20° C. to 60° C. for 6 hours to 15 days.

* * * * *